United States Patent [19]

Ishizuka et al.

[11] Patent Number: 5,145,988
[45] Date of Patent: Sep. 8, 1992

[54] PROCESS FOR PRODUCING HYDRAZONE DERIVATIVES

[75] Inventors: Makoto Ishizuka; Takashi Wakasugi, both of Iwaki, Japan

[73] Assignee: Kureha Chemical Industry Co., Ltd., Tokyo, Japan

[21] Appl. No.: 734,170

[22] Filed: Jul. 22, 1991

[30] Foreign Application Priority Data

Jul. 24, 1990 [JP] Japan .................... 2-195505

[51] Int. Cl.$^5$ .......................... C07C 261/00
[52] U.S. Cl. .................................. 560/159
[58] Field of Search .............. 560/159; 568/483

[56] References Cited

U.S. PATENT DOCUMENTS 4,113,733  9/1978  Kruger ................ 560/159
4,570,002  2/1986  Budai ................. 560/159

FOREIGN PATENT DOCUMENTS 929034  6/1963  United Kingdom ........ 568/483

OTHER PUBLICATIONS

*Chemical Abstracts*, vol. 96, No. 23, Jun. 7, 1982, Columbus, OH, U.S.A., Mitsubishi Chemical Ind., "Hydrazone Derivatives", p. 614, No. 199 074n.

*Chemical Abstracts*, vol. 105, No. 23, Dec. 8, 1986, Columbus, OH, U.S.A., Nasyrov et al., "Chloracetaldehyd acyl hydrazones", p. 555, No. 208 468c.

*Primary Examiner*—Michael L. Shippen
*Attorney, Agent, or Firm*—Cushman, Darby & Cushman

[57] ABSTRACT

A process for producing a hydrazone derivative represented by the following formula at a high purity at a high yield by decomposing monochloroacetaldehyde trimer into monochloroacetaldehyde monomer and then reacting the monomer with an alkyl carbazate in an organic solvent:

$$Cl-CH_2-CH=N-NH-COOR$$

(R represents an alkyl group).

7 Claims, No Drawings

PROCESS FOR PRODUCING HYDRAZONE DERIVATIVES

BACKGROUND OF THE INVENTION (1) Field of the Invention

The present invention relates to a process for producing a monochloroacetaldehyie (hereinafter referred to as MCA) alkoxycarbonylhydrazone.

The hydrazone derivative obtained in the present invention is useful as an intermediate for drugs, agricultural chemicals, etc.

(2) Description of the Prior Art

MCA alkoxycarbonylhydrazones are compounds known as intermediates for drugs, agricultural chemicals, etc. Various processes are known for the production of said compounds. For example, Japanese Patent Application Kokai (Laid-Open) No. 23974/1978 discloses a reaction of a halogenoacetaldehyde or an acetal form thereof with a lower alkyl carbazate in an aqueous medium. The reaction is carried out in a strongly acidic state of pH 1 or lower. As an improved process therefor, Japanese Patent Application Kokai (Laid-Open) No. 31649/1982 discloses conducting the above reaction with the pH of the reaction system being maintained at 3.5–5. All of these reactions are carried out in an aqueous medium because MCA is very unstable and quite easily polymerizable. In addition, MCA cannot be stored stably over a long period of time and accordingly, must be stored in an aqueous solution The transfer of the MCA dissolved in the aqueous solution into an organic layer is also very difficult. Generally, MCA is produced by chlorination of paraldehyde, acetaldehyde or vinyl acetate and immediately stored in an aqueous solution. The thus produced MCA, however, inevitably contains impurities such as dichloroacetaldehye and crotonaldehyde. Therefore, the hydrazone derivative produced according to the process disclosed in Japanese Patent Application Kokai (Laid-Open) No. 31649/1982 has a purity of about 95% at best. Thus, aqueous solutions of MCA produced by chlorination of paraldehyde, acetaldehyde, vinyl acetate or the like are not preferable as a starting material for producing a hydrazone derivative of high purity.

As mentioned above, MCA as a starting material for producing MCA hydrazone derivative is stored in approximately 40% aqueous solutions that contain impurities. Therefore, the reaction of MCA must be carried out in an aqueous medium. As a result, the hydrazone derivative crystals precipitated in the reaction contain water and are in the form of a very viscous lump, making the washing operation inefficient. It is difficult to separate the water and purify the crystals. Moreover, the hydrazone derivative obtained has a purity of 95% at best and a yield of 50–90%.

SUMMARY OF THE INVENTION

The present invention has been made in order to eliminate the above-mentioned drawbacks in hydrazone production.

An object of the present invention is to provide a process or producing a hydrazone derivative at a high purity.

Another object of the present invention is to provide a process for producing a hydrazone derivative at a high yield.

Still another object of the present invention is to provide a process for producing a hydrazone derivative, wherein the purification operation is easy.

The process of the present invention is characterized by reacting a MCA monomer obtained by depolymerization of MCA trimer, with an alkyl carbazate represented by the formula (I) in an organic solvent to obtain a MCA alkoxycarbonylhydrazone represented by the formula (II) at a high purity at a high yield:

$$H_2N-NH-COOR \qquad (I)$$

$$Cl-CH_2-CH=N-NH-COOR \qquad (II)$$

(in the above formulas, R represents an alkyl group).

DETAILED DESCRIPTION OF THE INVENTION

In the present invention, MCA trimer is used as one starting material in the production of MCA alkoxycarbonylhydrazone. Use of this MCA trimer has made the reaction of MCA possible in an organic solvent. MCA trimer is in the form of white crystals having a melting point of 87°–88° C. and can be produced by, for example, the process of Natterer [Monatsh. 3, p. 461–464 (1882)]. Specifically, it can be easily produced by dissolving a chloroacetaldehyde solution containing MCA as a main component in an organic solvent such as hexane and cyclizing MCA in the presence of sulfuric acid [Japanese Patent Application Kokai (Laid-Open) No. 223575/1990]. MCA trimer is stable and can be stored as is over a long period of time. In the present invention, the MCA monomer obtained by depolymerizing MCA trimer in the presence of an acid catalyst, is dissolved in an organic solvent and used for the reaction.

The alkyl carbazate used as another starting material in the present invention has no particular restriction as to the carbon atoms of the alkyl group. However, it is preferred to use an alkyl carbazate having an alkyl group of 1–6 carbon atoms. Particularly preferable alkyl carbazates are those having an alkyl group of 1–4 carbon atoms such as methyl carbazate, ethyl carbazate, propyl carbazate and butyl carbazate. The alkyl group may be, besides n-alkyl groups, a sec-alkyl group or a tert-alkyl group. These alkyl carbazates can generally be easily obtained by reacting hydrazine hydrate with an alkyl carbonate according to a known process.

In the present invention, the reaction of MCA monomer with an alkyl carbazate is effected in an organic solvent. Any organic solvent can be used as long as it dissolves the alkyl carbazate, and includes, for example, aliphatic hydrocarbons (e.g. hexane, heptane), alicyclic hydrocarbons (e.g. cyclohexane), aromatic hydrocarbons (e.g. benzene, toluene), carbon disulfide, carbon tetrachloride and diethyl ether. When one of these organic solvents is used, the MCA alkoxycarbonylhydrazone formed is precipitated successively. Such solvents as alcohols (e.g. methanol, ethanol), acetonitrile, ethyl acetate and tetrahydrofuran can also be used. When one of these solvents is used, the product is dissolved in the solvent. Therefore, it is necessary to remove the solvent by distillation to obtain the product.

In carrying out the present invention, MCA trimer is first decomposed into MCA monomer. Specifically, MCA trimer is heated to 120°–130° C. in the presence of an acid catalyst such as paratoluenesulfonic acid, whereby MCA is generated at a high purity. This MCA is dissolved in the above-mentioned organic solvent, and thereto is added alkyl carbazate directly or dissolved in the same organic solvent as is used for MCA. Alternatively, the MCA obtained by decomposition of MCA trimer may be added to an organic solvent solution of an alkyl carbazate. The proportion of the alkyl carbazate to MCA is 0.7-1.2 moles, preferably 0.8-1.1 moles of alkyl carbazate per 1 mole of MCA. Preferably, at least enough organic solvent is used to dissolve the alkyl carbazate substantially completely. When a solvent in which the product is precipitated is used, the amount of the solvent is preferably such that stirring is not made difficult by the precipitation of the product. The specific amount of the solvent differs to some extent depending upon the kind of solvent used. The solvent is used so as to give a solution containing 10-30% by weight (15-25% by weight in many cases) of MCA. In the reaction of MCA with an alkyl carbazate, no pH adjustment is required, unlike in the conventional reaction conducted in an aqueous medium.

The reaction temperature is generally −20° C. to 60° C. When the temperature is lower than −20° C, the reaction does not proceed favorably; when the temperature is higher than 60° C., the crystals formed are colored. The reaction temperature is preferably 0°-30° C. The reaction time is generally 10-120 minutes starting from the mixing of MCA with an alkyl carbazate, and preferably 30-60 minutes in many cases.

When a solvent which does not dissolve the hydrazone derivative is used, after the completion of the reaction, the precipitated hydrazone derivative is collected by filtration, followed by simply washing with the same solvent and drying to obtain a MCA alkoxycarbonyl hydrazone at a purity of 99% or more at a yield of 95% or more. When a solvent which is capable of dissolving the hydrazone derivative (e.g. alcohol, acetonitrile) is used, after the completion of the reaction, the reaction mixture is subjected to distillation under reduced pressure to remove the solvent to separate the product. The product is washed with a solvent which has low solvency for the product (e.g. hexane) to obtain the intended product at a purity of 99% or more at a yield of 95% or more, as in the above case.

The present invention is hereinafter described specifically with reference to Examples. However, the present invention is in no way restricted to these Examples.

In the following Examples, measurement of purity was made by internal standard gas chromatography.

EXAMPLE 1

A 100-ml distillation flask equipped with a thermometer was charged with 27.9 g of MCA trimer and paratoluenesulfonic acid as catalyst. The mixture was heated to 120° C. and 26.2 g of a distillate was obtained. The distillate was analyzed by gas chromatography. As a result, it was confirmed that the distillate was MCA having a purity of 99.8%.

The distillate was dissolved in carbon tetrachloride to prepare a solution containing 18% by weight of MCA. In a 100-ml three-necked flask equipped with a stirrer was charged 34.89 g of the solution [containing 6.28 g (0.08 mole) of MCA] and 8.33 g (0.08 mole) of ethyl carbazate.

The mixture was stirred at 20° C. for 1 hour. After the reaction was over, the formed crystals were collected by filtration, washed with carbon tetrachloride, and dried to obtain 12.87 g of white crystals of MCA ethoxycarbonylhydrazone having a purity of 99.7% and a melting point of 118°-119° C. The yield of the product was 97.4%.

COMPARATIVE EXAMPLE 1

A 40% aqueous MCA solution (pH<1), which is available on the market, was diluted with water to prepare an aqueous solution containing 18% by weight of MCA. 34.89 g of the aqueous solution [containing 6.28 g (0.08 mole) of MCA] was fed into a 100-ml three-necked flask provided with a stirrer. 8.33 g (0.08 mole) of ethyl carbazate was added. The mixture was subjected to reaction at 20° C. for 1 hour to obtain a precipitate in a form of a highly viscous lump. The precipitate was collected by filtration, washed repeatedly with water and hexane for purification, and dried to obtain 7.15 g of MCA ethoxycarbonylhyirazone having a purity of 95.6%. The yield of the product was 51.9%.

COMPARATIVE EXAMPLE 2

The procedure of Comparative Example 1 was repeated except that the pH of the aqueous MCA solution was adjusted to 4.0 prior to the reaction. The resulting MCA ethoxycarbonylhydrazone had a purity of 92.0% and gave a yield of 90.5%.

COMPARATIVE EXAMPLE 3

A 100-ml distillation flask equipped with a thermometer was charged with 27.9 g of MCA trimer and paratoluenesulfonic acid as catalyst. The mixture was heated to 120° C. and 26.3 g of a distillate was obtained. The distillate was analyzed by gas chromatography. As a result, it was confirmed that the distillate was MCA having a purity of 99.7%.

The distillate was dissolved in water to prepare an aqueous solution containing 18% by weight of MCA and the pH of the aqueous solution was adjusted to 4.0.

In a 100-ml three-necked flask equipped with a stirrer was charged 34.89 g of the solution [containing 6.28 g (0.08 mole) of MCA] and 8.33 g (0.08 mole) of ethyl carbazate. The mixture was stirred at 20° C. for 1 hour.

After the reaction was over, the obtained precipitate in a form of a highly viscous lump was isolated by filtration, washed with water and hexane for purification, and dried to obtain 12.07 g of white crystals of MCA ethoxycarbonylhyrazone having a purity of 99.4%. The yield of the product was 91.2%.

EXAMPLE 2

In the same manner as in Example 1, MCA trimer was subjected to distillation and the resulting distillate (MCA) was made into a hexane solution containing 14% by weight of MCA. 30.84 g of the solution [containing 4.32 g (0.055 mole) of MCA] was fed into a 100-ml three-necked flask with a stirrer. 5.72 g (0.055 mole) of ethyl carbazate was added. The mixture was subjected to reaction at 20° C. for 1 hour. After the completion of the reaction, the formed crystals were collected by filtration, washed with hexane, and dried to obtain 8.69 g of MCA ethoxycarbonylhydrazone having a purity of 99.2%. The yield of the product was 95.2%.

EXAMPLE 3

In the same manner as in Example 1, MCA trimer was subjected to distillation and the resulting distillate (MCA) was made into a hexane solution containing 20% by weight of MCA. 31.40 g of the solution [containing 6.28 g (0.08 mole) of MCA] was fed into a 100- ml three-necked flask with a stirrer. Thereto was added 7.20 g (0.08 mole) of methyl carbazate. The mixture was subjected to reaction at 20° C. for 1 hour. After the completion of the reaction, the formed crystals were collected by filtration, washed with hexane, and dried to obtain 11.90 g of MCA methoxycarbonylhydrazone having a purity of 99.2% and a melting point of 143°-144° C. The yield of the product was 98.0%.

EXAMPLE 4

In the same manner as in Example 1, MCA trimer was subjected to distillation and the resulting distillate (MCA) was made into a hexane solution containing 12% by weight of MCA. 39.25 g of the solution [containing 4.71 g (0.06 mole) of MCA] was fed into a 100-ml three-necked flask with a stirrer. 7.92 g (0.06 mole) of isobutyl carbazate was added. The mixture was subjected to reaction at 20° C. for 1 hour. After the completion of the reaction, the formed crystals were collected by filtration, washed with hexane, and dried to obtain 11.11 g of MCA isobutoxycarbonylhydrazone having a purity of 99.5% and a melting point of 118°-120° C. The yield of the product was 95.7%.

EXAMPLE 5

In the same manner as in Example 1, MCA trimer was subjected to distillation and the resulting distillate (MCA) was made into a hexane solution containing 12% by weight of MCA. 52.33 g of the solution [containing 6.28 g (0.08 mole) of MCA] was fed into a 100-ml three-necked flask with a stirrer. 9.44 g (0.08 mole) of isopropyl carbazate was added. The mixture was subjected to reaction at 20° C. for 1 hour. After the completion of the reaction, the formed crystals were collected by filtration, washed with hexane, and dried to obtain 13.77 g of MCA isopropoxycarbonylhydrazone having a purity of 99.6% and a melting point of 105°-107° C. The yield of the product was 96.0%.

EXAMPLE 6

In the same manner as in Example 1, MCA trimer was subjected to distillation and the resulting distillate (MCA) was made into a methanol solution containing 20% by weight of MCA. 37.30 g of the solution [containing 7.46 g (0.095 mole) of MCA] was fed into a 100-ml three-necked flask with a stirrer. 9.88 g (0.095 mole) of ethyl carbazate was added. The mixture was subjected to reaction for 1 hour. After the completion of the reaction, the reaction mixture was subjected to distillation under reduced pressure (20 mmHg) to remove the solvent, whereby crystals were precipitated. The crystals were washed with hexane and dried to obtain 14.98 g of MCA ethoxycarbonylhydrazone having a purity of 99.8%. The yield of the product was 95.6%.

EXAMPLE 7

MCA ethoxycarbonylhydrazone was synthesized in the same manner as in Example 2 except that the solvent (hexane) used in the MCA solution in Example 2 was changed to the various solvents shown in Table 1.

The purities and yields of the MCA ethoxycarbonylhydrazones obtained are shown in Table 1.

TABLE 1

| Solvent | Purity (%) | Yield (%) |
| --- | --- | --- |
| Cyclohexane | 99.3 | 96.4 |
| Heptane | 99.6 | 97.3 |
| Benzene | 99.4 | 95.8 |
| Toluene | 99.7 | 96.1 |
| Carbon disulfide | 99.5 | 95.6 |

TABLE 1-continued

| Solvent | Purity (%) | Yield (%) |
| --- | --- | --- |
| Diethyl ether | 99.6 | 96.3 |

EXAMPLE 8

MCA ethoxycarbonylhydrazone was synthesized in the same manner as in Example 6 except that the solvent (methanol) used in the MCA solution in Example 6 was changed to the various solvents shown in Table 2.

The purities and yields of the MCA ethoxycarbonylhydrazones obtained are shown in Table 2.

TABLE 2

| Solvent | Purity (%) | Yield (%) |
| --- | --- | --- |
| Acetonitrile | 99.2 | 97.4 |
| Ethanol | 99.7 | 96.8 |
| Ethyl acetate | 99.5 | 95.9 |
| Tetrahydrofuran | 99.4 | 97.1 |

In the present process, unstable MCA is once converted to its trimer, which is stable. The trimer is depolymerized into MCA when required for the process, and the resulting MCA is used as a starting material for the synthesis of MCA alkoxycarbonylhydrazone. Therefore, the synthesis of MCA alkoxycarbonylhydrazone, which has hitherto been possible only in the presence of an aqueous medium, is possible in an organic solvent. As a result, the present process, in contrast to the conventional process conducted in an aqueous medium, requires no pH adjustment in the reaction, requires no special recrystallization operation after the reaction, and can produce a MCA alkoxycarbonylhydrazone having a purity of 99% or more at a high yield. This process can be used advantageously in industry.

What is claimed is:

1. A process for producing a monochloroacetaldehyde alkoxycarbonylhydrazone represented by the formula (II), which comprises depolymerizing monochloroacetaldehyie trimer into monochloroacetaldehyie monomer and then reacting the monomer with an alkyl carbazate represented by the formula (I) in an organic solvent:

$$H_2N-NH-COOR \qquad (I)$$

$$Cl-CH_2-CH=N-NH-COOR \qquad (II)$$

(In the above formulas, R represents an alkyl group).

2. A process according to claim 1, wherein the depolymerization of monochloroacetaldehyde trimer is carried out by heating in the presence of an acid catalyst.

3. A process according to claim 1, wherein the organic solvent is a solvent capable of precipitating the formed monochloroacetaldehyde alkoxycarbonylhydrazone.

4. A process according to claim 3, wherein the organic solvent is selected from the group consisting of aliphatic hydrocarbons, alicyclic hydrocarbons, aromatic hydrocarbons, carbon disulfide, carbon tetrachloride and diethyl ether.

5. A process according to claim 1, wherein the organic solvent is a solvent capable of dissolving the formed monochloroacetaldehyde alkoxycarbonylhydrazone.

6. A process according to claim 5, wherein the organic solvent is selected from the group consisting of alcohols, acetonitrile, ethyl acetate and tetrahydrofuran.

7. A process according to claim 1, wherein the reaction of monochloroacetaldehyde monomer with an alkyl carbazate is carried out in an organic solvent at 0°-30° C. with no pH adjustment, with a molar ratio of 1 (monomer) to 0.8-1.1 (alkyl carbazate).

* * * * *